United States Patent
Swenson

(10) Patent No.: US 10,456,067 B2
(45) Date of Patent: Oct. 29, 2019

(54) BLOOD COLLECTION ASSEMBLY

(75) Inventor: Kirk D. Swenson, North Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 615 days.

(21) Appl. No.: 11/572,220

(22) PCT Filed: Jul. 20, 2005

(86) PCT No.: PCT/US2005/025765
§ 371 (c)(1),
(2), (4) Date: Aug. 26, 2008

(87) PCT Pub. No.: WO2006/014751
PCT Pub. Date: Feb. 9, 2006

(65) Prior Publication Data
US 2008/0319345 A1     Dec. 25, 2008

Related U.S. Application Data

(60) Provisional application No. 60/589,294, filed on Jul. 20, 2004.

(51) Int. Cl.
*A61B 5/15*     (2006.01)
*A61B 5/154*    (2006.01)

(52) U.S. Cl.
CPC .......... *A61B 5/15003* (2013.01); *A61B 5/154* (2013.01); *A61B 5/150267* (2013.01);
(Continued)

(58) Field of Classification Search
CPC .......... A61B 5/15049; A61B 5/150496; A61B 5/150473–150519; A61B 5/150267; A61B 5/150732
(Continued)

(56) References Cited

U.S. PATENT DOCUMENTS 4,155,350 A    5/1979   Percarpio
4,333,478 A    6/1982   Krieg
               (Continued)

FOREIGN PATENT DOCUMENTS

EP    0364777 A1    4/1990
EP    1433419 A1    6/2004
      (Continued)

OTHER PUBLICATIONS

PCT Search Report and Written Opinion.

*Primary Examiner* — Devin B Henson
*Assistant Examiner* — H. Q. Nguyen
(74) *Attorney, Agent, or Firm* — The Webb Law Firm

(57) ABSTRACT

A blood collection assembly includes a hub with a distal end, a proximal end, a hub outer surface and an internal opening extending therethrough. The assembly also includes a holder housing defining a receiving chamber and having a rearward end adapted to receive a sample collection tube within the chamber and a forward end including a receiving port extending into the chamber, where the receiving port receives a portion of the proximal end of the hub therein. An internal opening of the hub accommodates a puncturing element at the proximal end thereof for providing passage of a fluid therethrough, and the puncturing element contacts the sample collection tube. The hub and the holder housing include an interengaging structure extending substantially perimetrically therearound for axially locking the hub with the holder housing.

20 Claims, 14 Drawing Sheets

(52) U.S. Cl.
CPC .. *A61B 5/150396* (2013.01); *A61B 5/150496* (2013.01); *A61B 5/150572* (2013.01); *A61B 5/150633* (2013.01); *A61B 5/150671* (2013.01); *A61B 5/150732* (2013.01); *A61B 5/150778* (2013.01); *A61B 5/150816* (2013.01); *Y10T 29/49826* (2015.01)

(58) Field of Classification Search
USPC .............................. 600/576–582, 573, 575
See application file for complete search history.

(56) References Cited

U.S. PATENT DOCUMENTS

| | | | |
|---|---|---|---|
| 4,784,650 A | 11/1988 | Coburn | |
| 4,788,986 A | 12/1988 | Harris | |
| 4,822,343 A | 4/1989 | Beiser | |
| 4,834,715 A | 5/1989 | Hanifl | |
| 4,841,985 A | 6/1989 | Wanamaker | |
| 4,907,600 A | 3/1990 | Spencer | |
| 4,932,418 A | 6/1990 | Coburn | |
| 4,942,881 A | 7/1990 | Al-Sioufi | |
| 4,974,603 A | 12/1990 | Jacobs | |
| 4,984,580 A | 1/1991 | Wanamaker | |
| 4,993,426 A | 2/1991 | Spencer | |
| 5,066,286 A | 11/1991 | Ryan | |
| 5,066,287 A | 11/1991 | Ryan | |
| 5,069,225 A | 12/1991 | Okamura | |
| 5,117,837 A | 6/1992 | Wanamaker | |
| 5,143,083 A | 9/1992 | Al-Sioufi | |
| 5,181,524 A | 1/1993 | Wanderer | |
| 5,277,311 A * | 1/1994 | Hollister | ...................... 206/365 |
| 5,299,687 A | 4/1994 | Hanifl | |
| 5,456,265 A * | 10/1995 | Yim | .............................. 600/569 |
| 5,772,643 A * | 6/1998 | Howell | ............. A61M 25/0014 |
| | | | 138/155 |
| 6,059,737 A | 5/2000 | Crawford | |
| 6,152,913 A * | 11/2000 | Feith et al. | ................... 604/533 |
| 6,152,918 A * | 11/2000 | Padilla et al. | .................. 606/15 |
| RE37,908 E | 11/2002 | Kinsey | |
| 6,558,365 B2 | 5/2003 | Zinger | |
| 6,709,428 B2 | 3/2004 | Sagstetter | |
| 6,979,307 B2 | 12/2005 | Beretta | |
| 7,147,608 B2 | 12/2006 | Higaki | |
| 7,575,548 B2 * | 8/2009 | Takemoto | .......... A61B 1/00087 |
| | | | 600/104 |
| 2001/0014792 A1 * | 8/2001 | West et al. | ..................... 604/239 |
| 2002/0169408 A1 | 11/2002 | Beretta | |
| 2003/0093009 A1 | 5/2003 | Newby | |
| 2004/0071786 A1 | 4/2004 | Grippi | |
| 2005/0080385 A1 | 4/2005 | Lichtenberg | |
| 2012/0277769 A1 * | 11/2012 | Cabrera | ................. A61B 17/04 |
| | | | 606/147 |

FOREIGN PATENT DOCUMENTS

| WO | 90/07903 A1 | 7/1990 |
|---|---|---|
| WO | 2004/093938 A2 | 11/2004 |
| WO | WO2006014751 A2 | 2/2006 |

* cited by examiner

BLOOD COLLECTION ASSEMBLY

The present application claims priority to U.S. Provisional Application No. 60/589,294 filed on Jul. 20, 2004.

BACKGROUND OF THE INVENTION

1. Field of the Invention

The present invention relates generally to a medical needle device and assembly for use in connection with blood collection procedures, such as a blood collection assembly that provides a snap fit connection between various components of the assembly.

2. Description of Related Art

Disposable medical needle devices having piercing elements are typically used for administrating a medication or withdrawing a fluid, such as blood, from the body of the patient. Such piercing elements include blood collection needles, fluid handling needles and assemblies thereof. Current medical practice often requires that fluid collection containers and needle assemblies used in such devices be inexpensive and readily disposable. Often, existing blood collection devices employ some form of a durable reusable holder on which detachable and disposable needle assemblies and fluid collection containers are mounted. A blood collection system of this nature may be assembled prior to use and then disassembled after use.

Known blood collection systems typically include a double-ended needle assembly attached with a holder supporting the needle assembly, with the holder capable of accommodating an evacuated fluid collection tube therein. The double-ended needle assembly includes a hub having a bore therethrough, with a needle cannula extending through the bore of the hub. The hub of the needle assembly is received through an opening at one end of the holder and maintained therein, such that a first or distal end of the needle extends outward from the holder for puncturing the vein of a patient. At the opposite end, a non-patient end of the needle extends into the hollow body. To assemble the blood collection system, the needle assembly is inserted into the housing and the evacuated fluid collection tube is partially inserted through the open end of the hollow body. To draw a blood specimen from the patient using one of these systems, the distal exposed end of the needle is inserted into a patient's vein, and the collection tube is fully inserted into the holder until the second or proximal end of the needle pierces a puncturable stopper of the fluid collection tube, thereby allowing fluid communication between the interior of the fluid collection tube and the bore of the needle. Blood will then be drawn through the needle into the evacuated fluid collection tube based on the negative pressure therein. After drawing a specimen, the blood collection tube is removed so that blood contained therein may be analyzed, and the needle assembly detached for disposal.

A prior art blood collection device known in the art is disclosed in U.S. Pat. No. 5,066,287 to Ryan. This patent discloses a rear adapter assembly used as part of a blood collection set. The rear adapter assembly includes a rear blood tube holder and a male connector that is inserted into the holder. The male connector includes a ratcheted ramp with a plurality of ratchet teeth that engage with an annular internal ratchet located within the holder. In particular, the annular internal ratchet is provided on a holder ramp formed in the front wall of the holder. The ratcheting connection between the male connector and the holder provides a permanent connection between these two elements.

Another blood collection device known in the art is disclosed in U.S. Pat. No. 5,117,837 to Wanamaker et al. The patent is directed to a blood collection device that is generally comprised of a needle assembly and a needle holder for use with an evacuated sample collection tube. The needle assembly includes a hub which is connected to the holder through an adapter. The adapter and hub are connected together by a threaded connection, and the adapter includes a crown defining a plurality of serrated teeth. The serrated teeth on the crown are adapted to cooperate with the serrated teeth formed on a lid, which covers the distal end of the holder. The adapter engages with the lid covering the distal end of the holder.

Yet another blood collection device known in the art is disclosed in U.S. Pat. No. 5,066,286 to Ryan. This patent discloses a luer adapter assembly having a male connector and a rear blood tube holder. The rearward end of the male connector includes a hollow middle portion defining a groove, which snap-fits into the forward end of the holder such that the male connector is permanently installed in the rear blood tube holder. The connector and the holder have an interrupted contacting surface, which permits slight movement between the elements. The male connector also includes a plurality of longitudinally extending protrusions spread about the connector and terminates with a stop collar. The protrusions engage with respective longitudinal grooves in the holder in order to prevent unwanted rotation of the male connector relative to the rear tube holder.

Prior art devices such as those noted typically involve complex engagement systems between the hub and/or the male luer connector and the holder. Such devices are often difficult to align, engage and otherwise assemble due to the structural limitations of the fittings.

SUMMARY OF THE INVENTION

A need exists for a blood collection assembly that includes the requisite components, where these components are easily manufactured, engaged and assembled in a safe and efficient manner.

Accordingly, an embodiment of the present invention provides a blood collection assembly comprising a holder housing defining a receiving chamber and including a rearward end adapted to receive a sample collection tube within the chamber and a forward end including a receiving port extending into the chamber. The assembly further comprises a hub including a hub outer surface extending between a distal end and a proximal end, an internal opening extending therethrough and a puncturing element at the proximal end thereof. The hub is received within the receiving port of the holder housing such that at least a portion of the hub outer surface engages a corresponding interior surface of the receiving port. The hub is maintained within the receiving port through interfering structure extending substantially perimetrically between the hub outer surface and the interior surface of the receiving port. In this manner, a snap-fit engagement axially locks the hub to the holder housing with the puncturing element of the hub extending through the receiving port and into the chamber of the holder housing for contact with a sample collection tube received within the chamber. The engagement between the hub outer surface and the corresponding receiving port interior surface provides support against torque applied to the distal end of the hub, preventing release of the snap-fit engagement established through the interfering structure between the hub outer surface and the receiving port interior surface.

Desirably, the hub includes a needle cannula mounted through the internal opening of the hub. The needle cannula includes a forward intravenous end with a puncture tip extending from the distal end of the hub and a rearward non-patient end extending from the proximal end of the hub, with the non-patient end comprising the puncturing element. Alternatively, the distal end of the hub may include a mating surface adapted to engage a medical device having a complimentary mating surface, such as a luer adapter.

In certain embodiments, the hub may include an annular protrusion, such as an annular rib, extending substantially perimetrically about the hub outer surface at a location between the distal and proximal ends of the hub. The receiving port can include a corresponding annular groove extending perimetrically within the interior surface of the receiving port, for mating with the annular protrusion of the hub.

Moreover, the assembly may include structure for preventing rotational movement of the hub within the receiving port. For example, the hub outer surface may comprise an anti-rotation element to prevent rotational movement of the hub within the receiving port. For example, the hub outer surface may include a nub extending from the outer surface at the proximal end, and the receiving port may be sized and shaped so as to receive and substantially abut the nub, such as through a notch portion configured to receive and substantially abut an outer surface of the nub. Moreover, the outer surface of the nub may be rounded and configured for ease of insertion within and abutment against a complimentary rounded internal surface of the notch portion of the receiving port.

In one particular embodiment, the hub includes a needle cannula having an intravenous end with a puncture tip extending from the distal end thereof, with the anti-rotation element providing a mechanism for properly aligning the hub within the receiving port of the holder so as to orient the puncture tip at the intravenous end of the needle cannula to a predetermined position, such as a bevel up orientation. Also, the rearward end of the holder housing may include a pair of flanges extending from opposing sides thereof and a bottom surface of the holder housing is configured to rest on the patient's skin. As such, the anti-rotation element may be adapted to align the bevel of the needle to a predetermined position with respect to the pair of flanges and the bottom surface of the holder housing.

It is further contemplated that the needle assembly may include shield in pivotable engagement with the hub and/or the holder housing, with the shield being adapted for pivotal movement to encompass the puncture tip of the needle cannula. A removable packaging cover may also cover the puncture tip of the needle cannula with the hub attached to the holder housing prior to use, and a rear cap element may be removably attached with the rearward end of the holder housing to seal the receiving chamber of the holder housing.

In a further embodiment, a blood collection assembly comprises a needle cannula having an intravenous end with a bevel puncture tip and a non-patient end mounted to a hub, the hub extending between a distal end and a proximal end and including an anti-rotation element extending from an outer surface thereof. A holder housing defines a receiving chamber, and includes a rearward end adapted to receive a sample collection tube within the chamber and a forward end including a receiving port extending therethrough and configured to receive at least a portion of the hub in a snap fit engagement therein. The receiving port includes structure corresponding to the anti-rotation element of the hub for engagement therewith to limit or prevent rotational movement of the hub with respect to the holder housing about a longitudinal axis defining the blood collection assembly. The hub and the receiving port include interengaging structure for axially locking the hub with the holder housing with the anti-rotation element of the hub contacting the corresponding structure of the receiving port to align the hub and the needle cannula to a predetermined position and prevent rotation of the hub with respect to the holder housing about the longitudinal axis. For example, the hub may include a protrusion extending substantially perimetrically about the outer surface at the proximal end and the receiving port may include a groove extending substantially perimetrically within the receiving port, with the protrusion of the hub adapted for locking engagement within the groove.

The rearward end of the holder housing may include at least one flange for resisting rolling of the holder housing on a flat surface thereby defining an upper surface of the holder housing. In this manner, insertion of the anti-rotation element within the receiving port substantially aligns the bevel of the cannula with the upper surface of the holder housing. A shield may further be provided in pivotable engagement with the hub and/or the holder housing, for pivotal movement to encompass the intravenous end of the needle cannula.

In yet a further embodiment, a method of attaching a needle assembly with a holder housing is provided. The method involves providing a needle assembly comprising a needle cannula having an intravenous end with a bevel puncture tip and a non-patient end mounted to a hub. The hub extends between a distal end and a proximal end, with a protrusion extending substantially perimetrically about an outer surface at the proximal end and an anti-rotation element extending from the outer surface at the proximal end. A holder housing defines a receiving chamber and includes a rearward end adapted to receive a sample collection tube within the chamber and a forward end including a receiving port extending therethrough and configured to receive at least a portion of the proximal end of the hub therein. The receiving port includes an internal surface for mating with said protrusion of the hub and a notch portion for engagement with the anti-rotation element of the hub. The proximal end of the hub is inserted into the receiving port of the holder housing such that the protrusion of the hub engages the corresponding mating internal surface of the receiving port substantially around an entire contacting surface therebetween to axially lock the hub with the holder housing. In this manner, insertion of the anti-rotation element within the receiving port aligns the hub, and therefore, the needle cannula to a predetermined position. Desirably, the anti-rotation element comprises a nub extending from a surface of the hub in alignment with the bevel. As such, insertion involves aligning the nub with the notch portion, thereby aligning the bevel to a predetermined position. Moreover, insertion of the hub within the receiving port may provide a tactile indication that the hub is axially locked with the holder housing through the interengaging structure.

Further details and advantages of the present invention will become apparent from the following detailed description read in conjunction with the drawings, wherein like parts are designated with like reference numerals.

DETAILED DESCRIPTION

Figure 1:
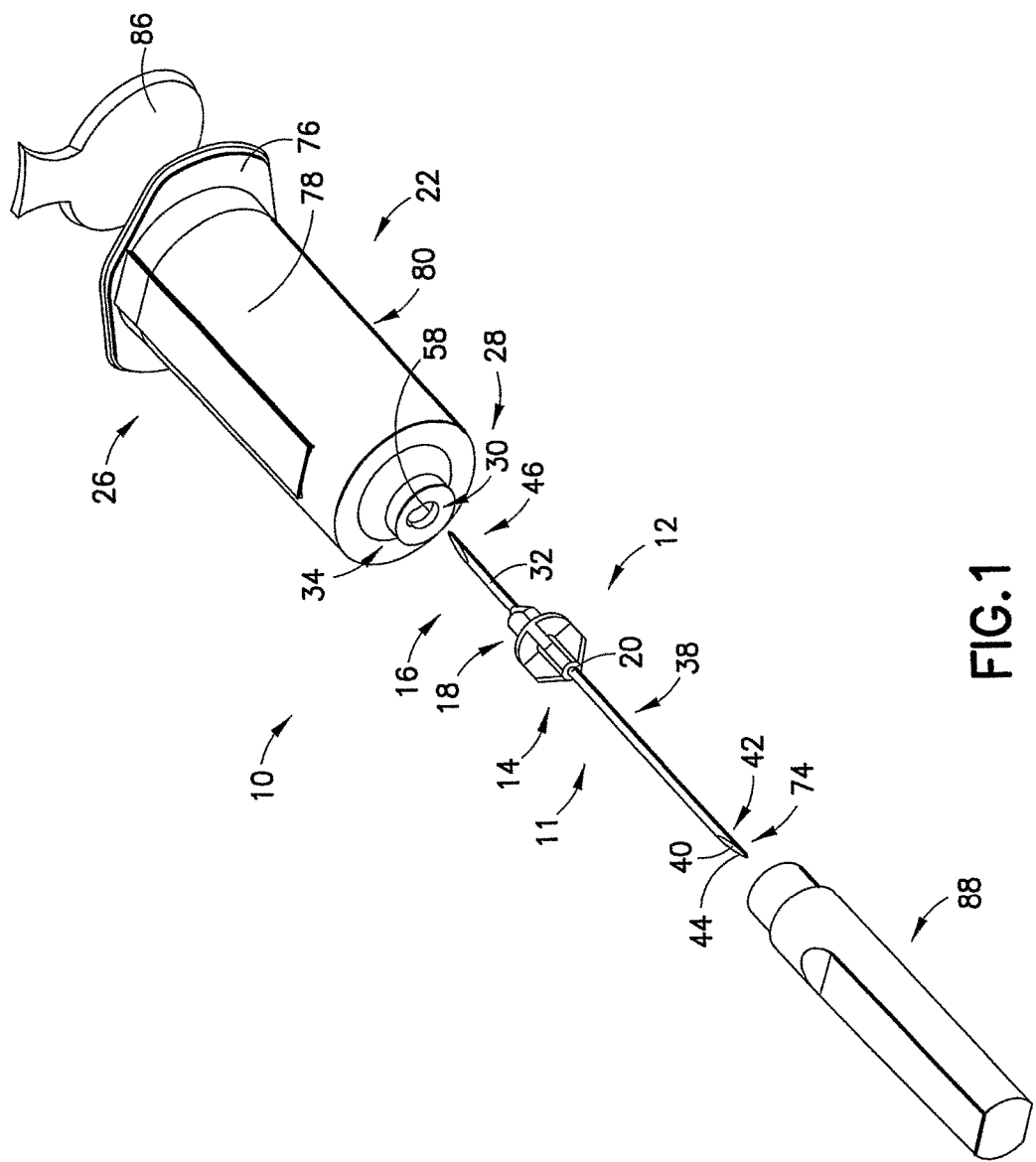
FIG. 1 is a perspective and exploded view of a blood collection assembly in accordance with and embodiment of the present invention.
Figure 2:
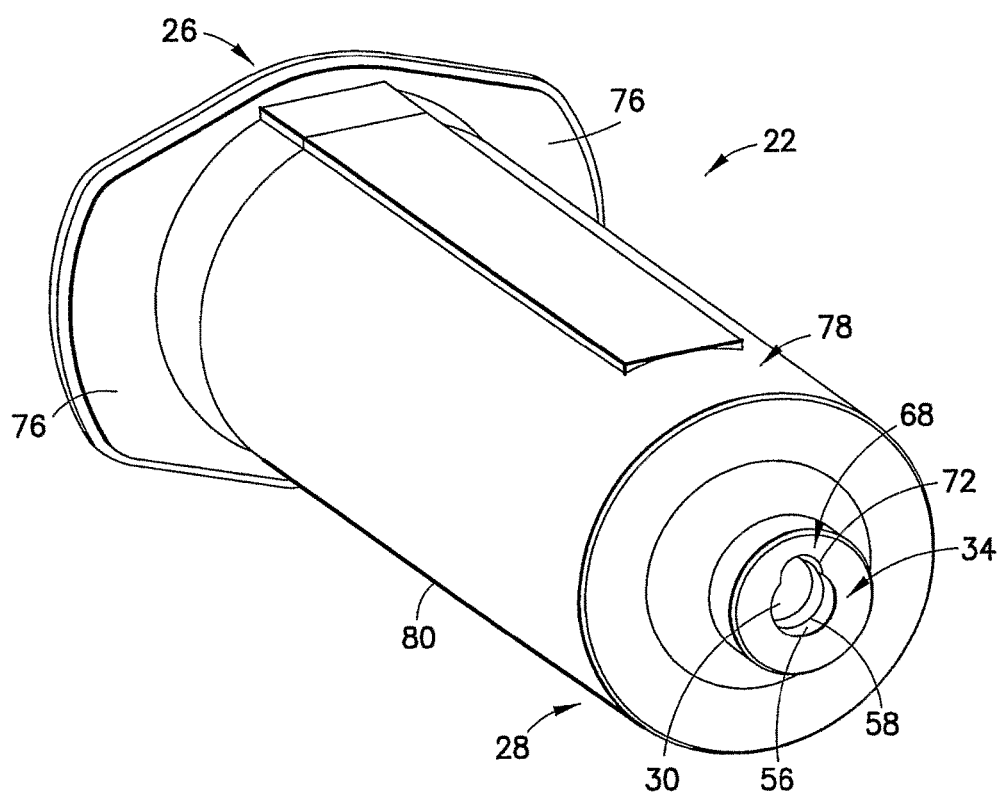
FIG. 2 is a perspective view of a holder housing of the blood collection assembly of FIG. 1.
Figure 3:
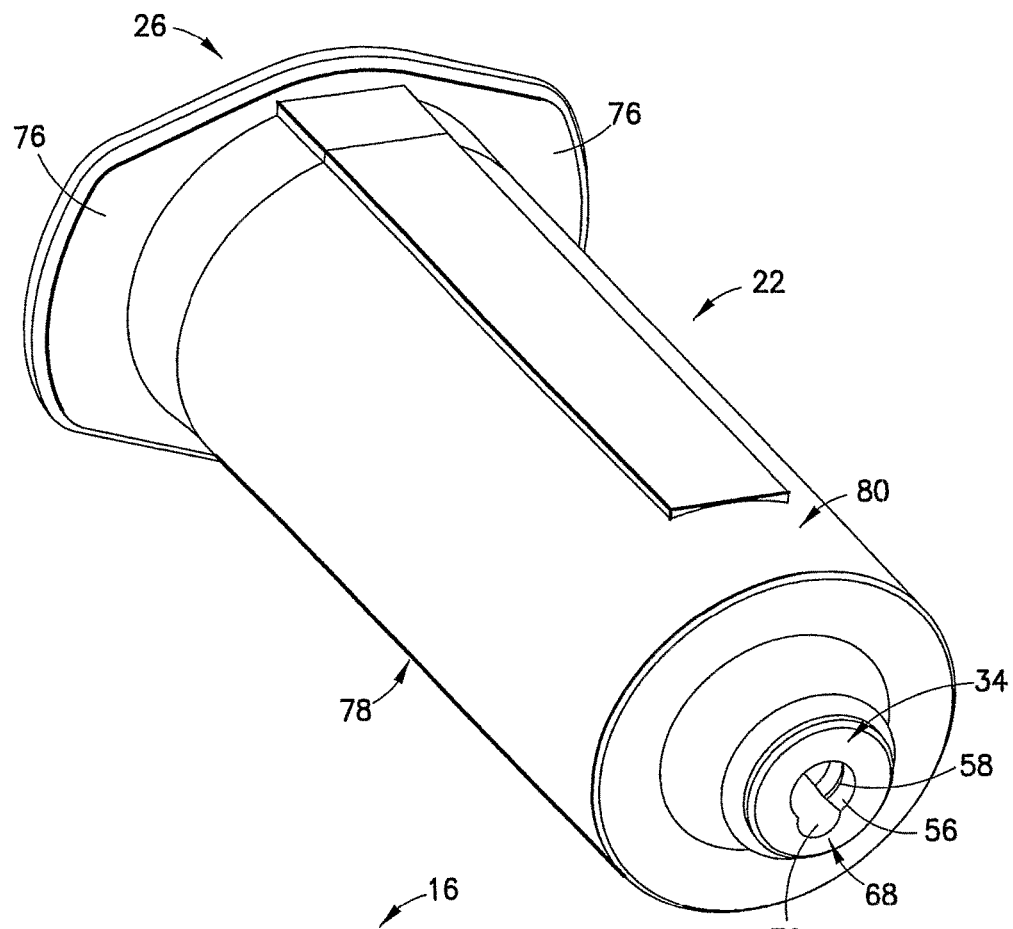
FIG. 3 is a further perspective view of the bottom of the holder housing of FIG. 2.

For purposes of the description hereinafter, the terms "upper", "lower", "right", "left", "vertical", "horizontal", "top", "bottom", "lateral", "longitudinal" and derivatives thereof shall relate to embodiments of the invention as they are oriented in the drawing figures. However, it is to be understood that these embodiments may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

In the following description and accompanying drawings, the term "distal" refers to the forward or patient side of the device, and the term "proximal" refers to the rearward or the non-patient side of the device, respectively. These designations will become apparent from the following detailed description.

Referring generally to the figures, a blood collection assembly 10 in accordance with an embodiment of the present invention is illustrated. The blood collection assembly 10 may be used, for example, in phlebotomy (i.e., blood collection) procedures and is designed in such an instance to allow and facilitate easy and efficient connection between the various components and sub-components of the blood collection assembly 10, as discussed hereinafter.

Referring to FIGS. 1-9, one embodiment of the blood collection assembly 10 will be discussed. The principle of operation of the blood collection assembly 10 of FIGS. 1-7 is illustrative of all the embodiments of the blood collection assembly 10 to be discussed herein. The blood collection assembly 10 is generally comprised of a needle assembly 11 attached to a holder housing 22. The needle assembly 11 includes a hub 12, with the hub 12 having a distal end 14, a proximal end 16, a hub outer surface 18 and an internal opening 20 extending through the hub 12.

Figure 6:
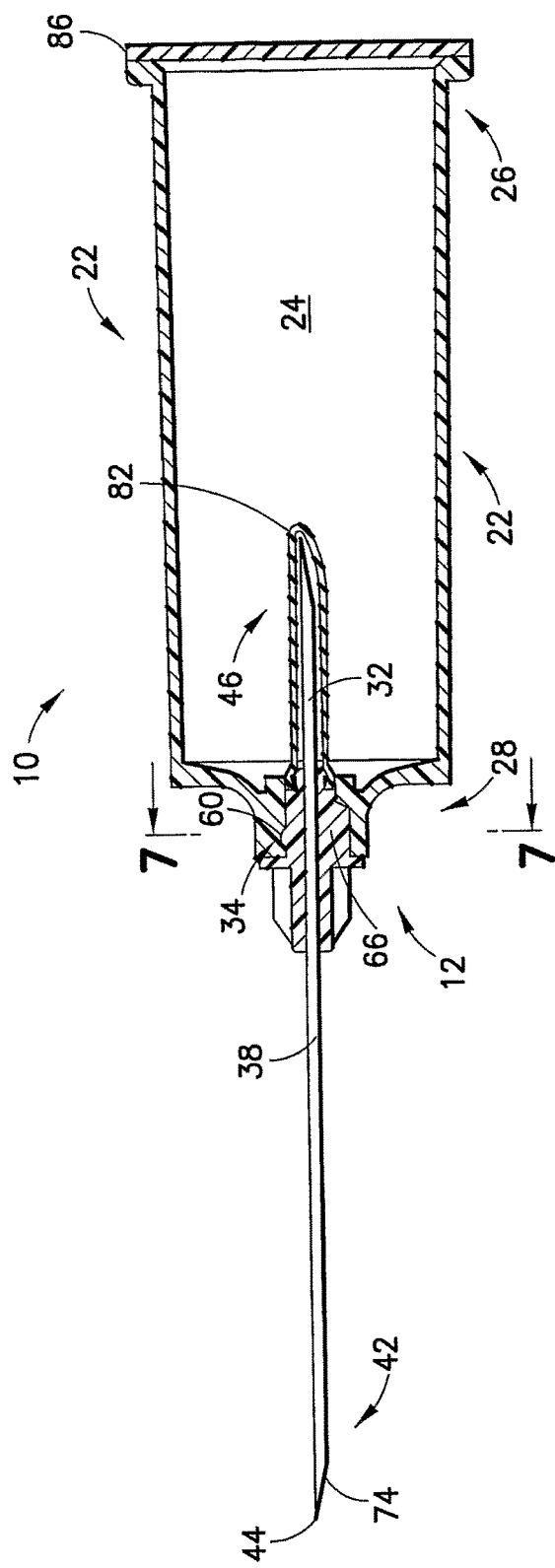
FIG. 6 is a side sectional view of the engaged assembly of FIG. 5.
Figure 7:
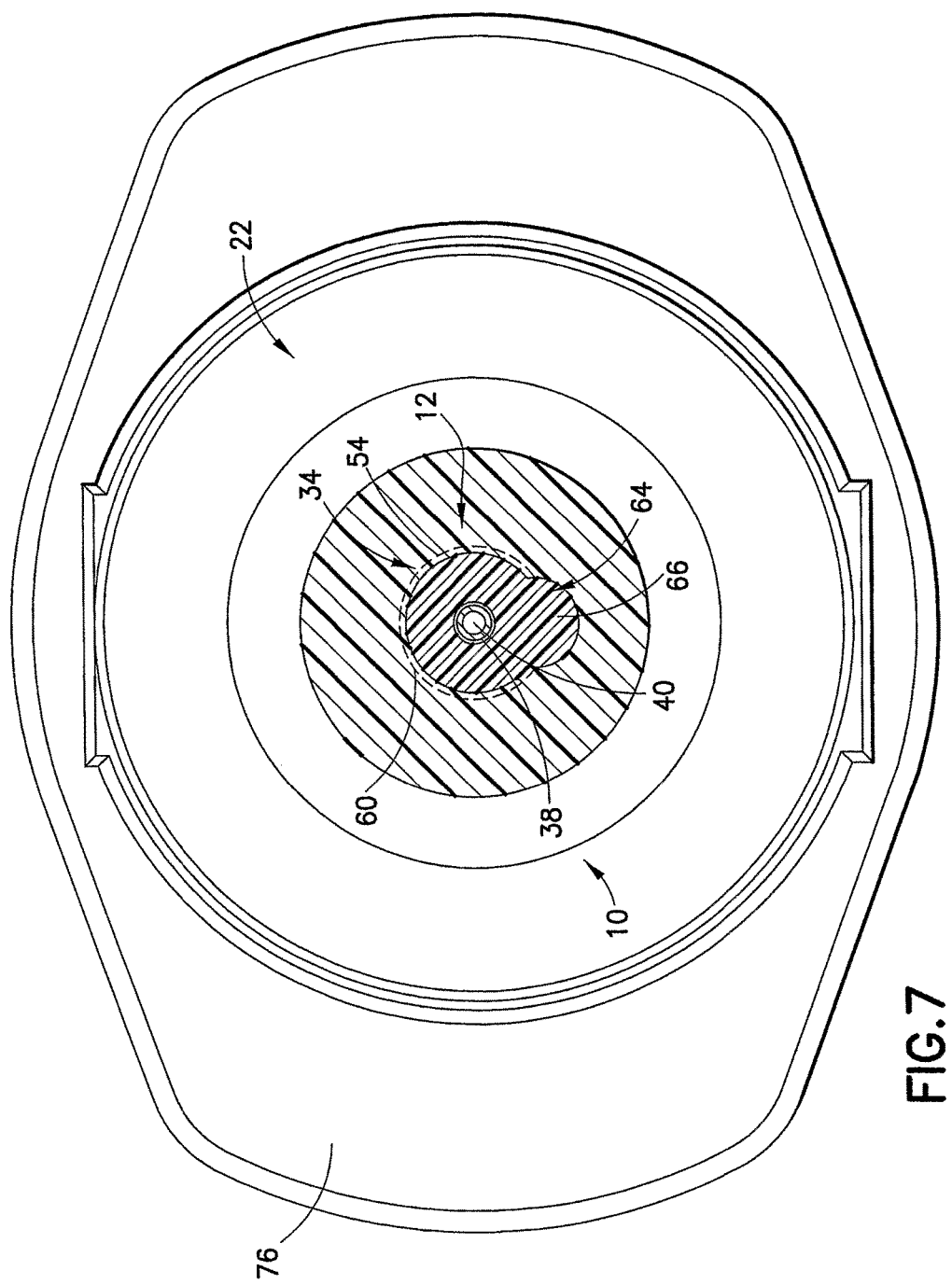
FIG. 7 is a plan sectional view taken along lines 7-7 in FIG. 6.

The hub 12 includes a puncturing element positioned near the proximal end 16 of the hub 12 for the passage of fluid therethrough, such as blood and the like. The puncturing element 32, in this embodiment, is adapted for contacting and piercing a sample collection tube during use, as will be discussed in more detail herein. Desirably, the needle assembly 11 includes a needle cannula 38 mounted through the internal opening 20 of the hub 12. The needle cannula 38 is generally a hollow needle structure having an internal lumen 40, and extends between a distal or forward end 42 establishing an intravenous or patient needle end having a puncture tip 44 and a proximal or rearward non-patient end 46. Desirably, the forward end 42 of the needle cannula 38 extends from the distal end 14 of the hub 12, and the proximal or rearward end 46 of the needle cannula 38 extends from the proximal end 16 of the hub 12. The rearward non-patient end 46 of the needle cannula 38 comprises the puncturing element 32 for contacting the sample collection tube. As shown in FIG. 6, the hub 12 may also include an elastomeric sleeve 82 extending from the proximal end 16 about the non-patient end 46 of the needle cannula 38. This elastomeric sleeve 82 acts as a valve for maintaining fluid within needle cannula during use of the blood collection assembly 10, and is adapted to be pierced by the non-patient end 46 of the needle cannula 38 during use, as is known in the art.

The blood collection assembly 10 also includes a holder housing 22, which defines a receiving chamber 24. The holder housing has a rearward end 26 for receiving a sample collection tube (not shown) within the chamber 24, and a forward end 28 with a receiving port 30 extending therethrough, establishing a pathway through the holder housing 22 into the receiving chamber 24. The receiving port 30 is sized and shaped so as to receive at least a portion of the proximal end 16 of the hub 12 of the needle assembly 11 therein.

The blood collection assembly 10, in accordance with an embodiment of the present invention, includes interengaging structure 34 between the hub 12 and the holder housing 22. This interengaging structure 34 is used to axially lock the hub 12 with the holder housing 22. In particular, this interengaging structure 34 provides for a "snap fit" between the hub 12 and the holder housing 22, such that the hub 12 may be easily attached to the holder housing 22 through an axial attachment along the longitudinal axis of the blood collection assembly 10 as opposed to a threaded or screw-on type attachment as is common within the art, thereby facilitating easy alignment and manipulation, and in many instances without the need for additional structure. Desirably, the interengaging structure 34 extends substantially around contacting or mating surfaces between the hub 12 and the holder housing 22. This interengaging structure 34 is adapted to axially lock the hub 12 and the holder housing 22.

In particular, the hub 12 desirably includes a protrusion 54 that extends substantially perimetrically about the hub outer surface 18 at the proximal end 16 of the hub 12. The receiving port 30 of the holder housing 22 includes a corresponding surface 56 for mating with this protrusion 54 on the hub 12. Accordingly, when the protrusion 54 is engaged with the corresponding surface 56, the hub 12 is axially locked with respect to the holder housing 22. The corresponding surface 56 includes a groove 58 that extends substantially perimetrically within the receiving port 30. Therefore, the protrusion 54 is sized and shaped so as to lockably engage with this groove 58. For example, the protrusion 54 may be an annular rib 60, which mates with the groove 58.

The blood collection assembly 10 may also include structure that limits and, in some cases, prevents rotational movement of the hub 12 when positioned in the receiving port 30 of the holder housing 22. In a preferred embodiment, the hub outer surface 18 includes an anti-rotation element 64 positioned adjacent the proximal end 16 of the hub 12. In addition, the receiving port 30 of the holder housing 22 is sized and shaped so as to receive and substantially abut the anti-rotation element 64 in an interference engagement which prevents rotational movement of the hub 12 within the receiving port 30 of the holder housing 22.

When used in connection with the above-discussed embodiment including a needle cannula 38 extending through the hub 12, the insertion of the anti-rotation element 64 within the receiving port 30 of the holder housing 22 aligns the hub 12. Accordingly, since the needle cannula 38 is fixed with respect to the hub 12, insertion of the anti-rotation element 64 also aligns the needle cannula 38 to a predetermined position with respect to the holder housing 22. In such an embodiment, insertion of the anti-rotation element 64 within the receiving port 30 occurs during the assembly process prior to the snap-fit engagement, thereby providing a mechanism for aligning the needle cannula 38 to the desired predetermined orientation before the hub 12 is snap fit into the holder housing 22.

In one preferred embodiment, the anti-rotation element 64 includes a nub 66 that extends generally longitudinally along the hub outer surface 18 from the proximal end 16 of the hub 12. In addition, the receiving port 30 includes a notch portion 68 for receiving and abutting against an outer surface 70 of the nub 66. The outer surface 70 of the nub 66 may be, for example, rounded for appropriate insertion within and abutment against a complimentary rounded internal surface 72 of the notch portion 68. Accordingly, the anti-rotation structure established through anti-rotation element 64 prevents rotation of the hub 12 with respect to the holder housing 22, as well as the assists in the alignment of the needle cannula 38. For example, in certain embodiments, the needle cannula 38 may include a bevel 74. It is oftentimes desirable to orient the bevel into an appropriate position during use of the blood collection assembly 10, such as in a "bevel up" orientation to assist in venipuncture. Desirably, the nub 66 extends from the hub 12 in longitudinal alignment with this bevel 74, such that insertion of the nub 66 within the notch portion 68 aligns the bevel 74 to a predetermined position.

Figure 4:
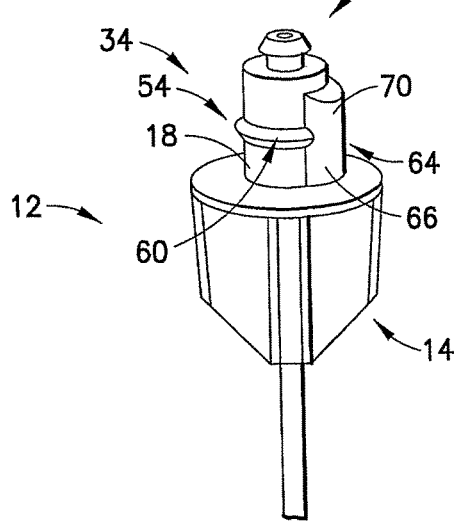
FIG. 4 is a perspective view of a hub of the blood collection assembly of FIG. 1.
Figure 5:
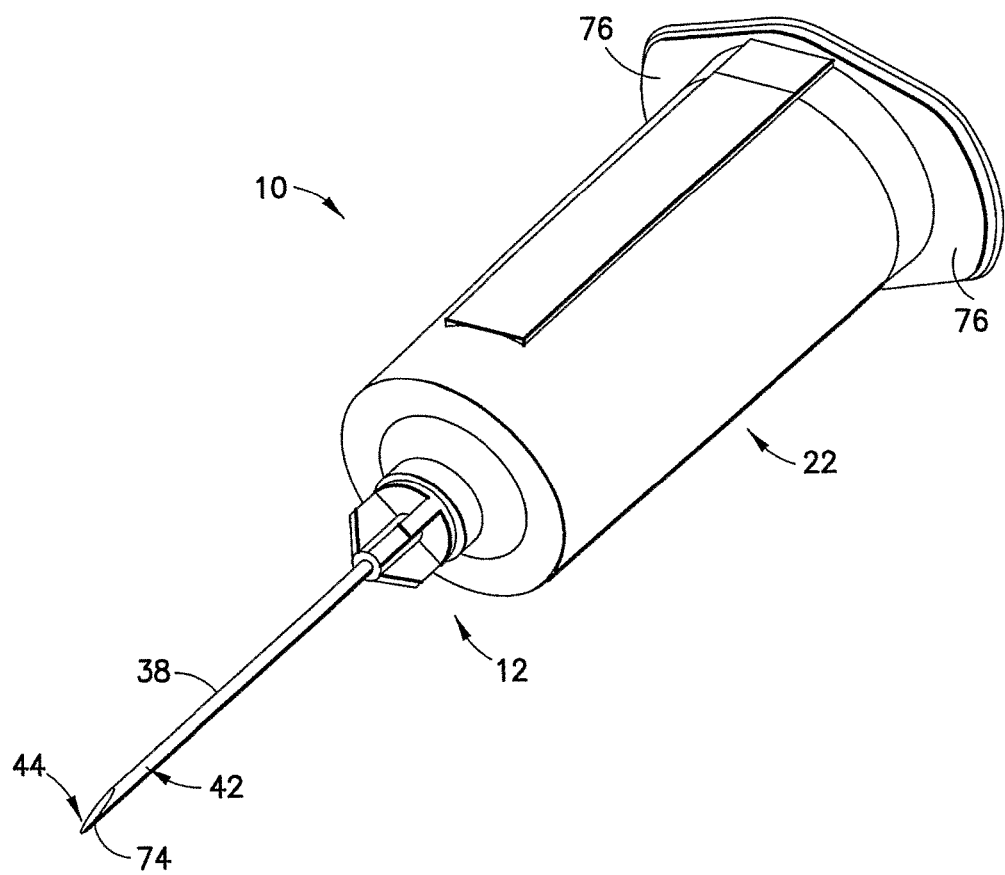
FIG. 5 is a perspective view of a needle assembly engaged with a holder housing.

The nub 66 may be located adjacent the annular rib 60 or, in another embodiment, desirably bisects annular rib 60 as shown in FIG. 4. In this manner, continuous contact is achieved perimetrically between the contacting surfaces of the hub 12 and the holder housing 22 establishing the axial lock and the rotational fixation therebetween.

The rearward end 26 of the holder housing 22 may also include a flange 76. This flange 76 resists rolling of the holder housing 22 on a flat surface, which thereby defines an upper surface 78 of the holder housing 22. Therefore, when the nub 66 of the holder 12 is inserted within the notch portion 68 of the holder housing 22, the bevel 74 of the needle cannula 38 is substantially aligned with the upper surface 78 of the holder housing 22. It is also envisioned that the rearward end 26 of the holder housing 22 includes a pair of flanges 76 that extend from opposing sides of the holder housing 22, such that a bottom surface 80 of the holder housing 22 may rest upon a patient's skin. In addition, with respect to the orientation of the bevel 74 of the needle cannula 38, the aforementioned arrangement may achieve a bevel orientation of between about 60 degrees and about 120 degrees from the flanges 76.

In another embodiment, the assembly 10 may include a cap element 86 that is removably attached with the rearward end 26 of the holder housing 22. Through the attachment of this cap element 86 with the holder housing 22, the receiving chamber 24 is sealed from the outside environment. The cap element 86 may be adhered or attached directly to the rearward end 26 of the holder housing 22, for example through an appropriate adhesive. It is further contemplated that the cap element 86 may be affixed at the rearward end 26 through a mechanical engagement, such as through interfering structure between the cap element 86 and the holder housing 22. For example, cap element 86 may include an annular rib which snap fits within a groove within the interior surface of the holder housing 22 at the rearward end thereof. Further, the blood collection assembly 10 may be hermetically sealed with an enclosure 88 after the hub 12 has been attached to the holder housing 22 through the interengaging structure 34. In this manner, blood collection assembly 10 can be provided as a completely assembled structure ready for use in a single pre-packaged assembly.

It is envisioned that a tactile indication may be provided during insertion of the hub 12 into the holder housing 22, where this tactile indication provides indication that the hub 12 is axially locked with the holder housing 22 through the interengaging structure 34. Such an arrangement ensures that the holder housing 22 and the hub 12 are appropriately and effectively axially locked.

Figure 10:
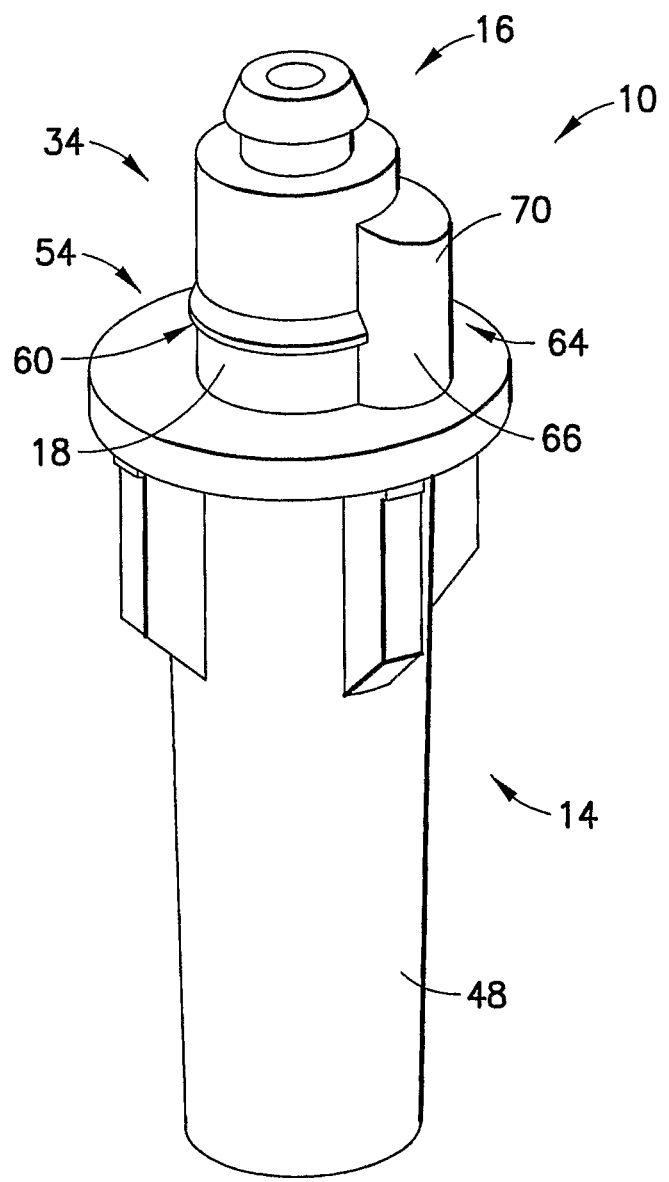
FIG. 10 is a perspective view of a hub with a tapered mating surface in accordance with a further embodiment.
Figure 11:
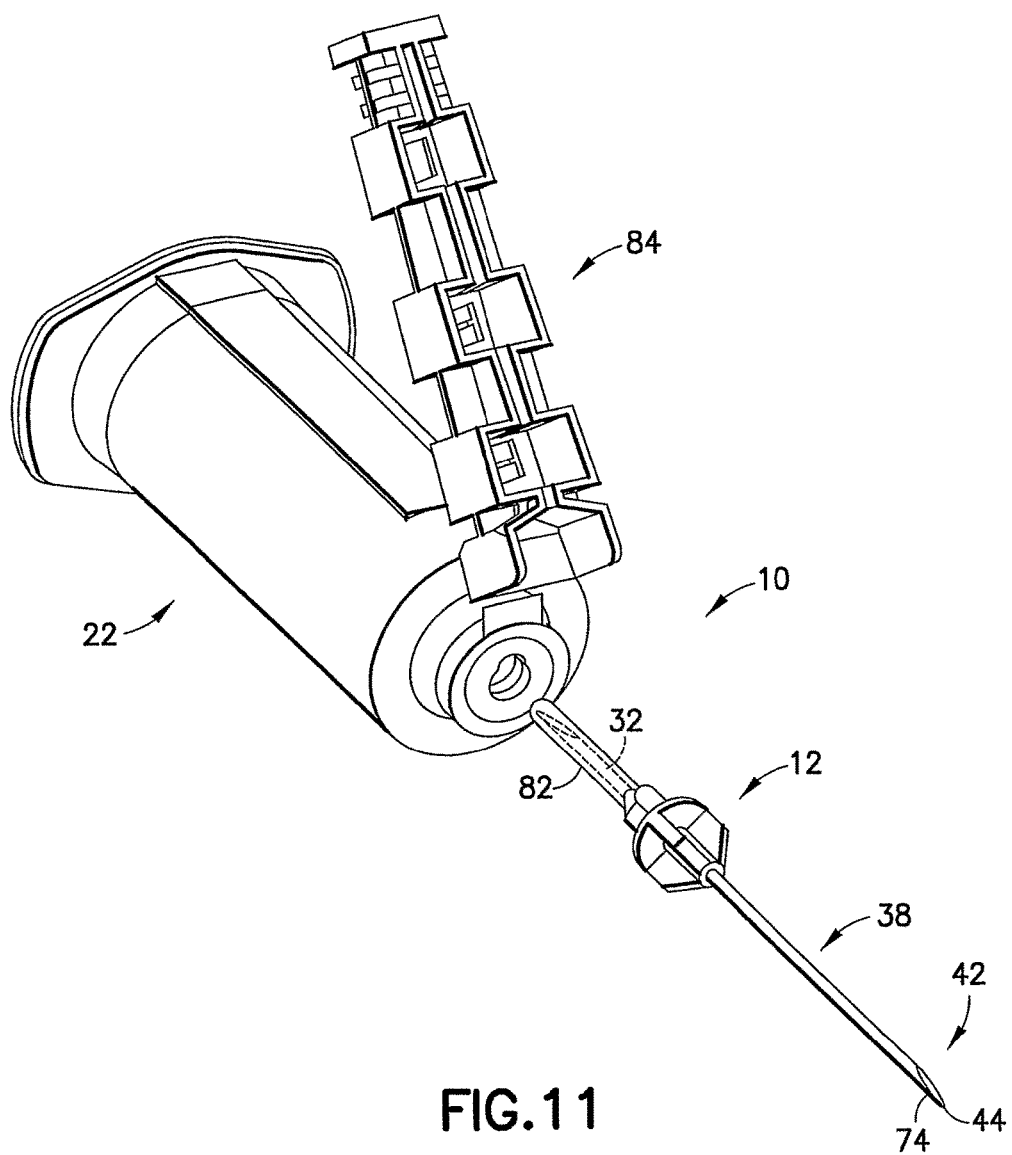
FIG. 11 is an exploded perspective view of a blood collection assembly and a pivotal shield in accordance with a further embodiment.

In another embodiment, as illustrated in FIG. 10, the hub 12 may include a tapered mating surface 48 extending from the distal end 14 of the hub 12. This tapered mating surface 48 is adapted to engage a separate medical device (not shown), which includes an interengaging and complimentary tapered mating surface. This arrangement is often referred to as a "luer" fitting, as is known in the art. Further, in this embodiment, the tapered mating surface 48 of the hub 12 may be removably lockable with the complimentary taped mating surface of the medical device. Accordingly, either of the tapered mating surfaces of the hub 12 or the medical device would include appropriate structure to effect this locking arrangement.

Figure 12:
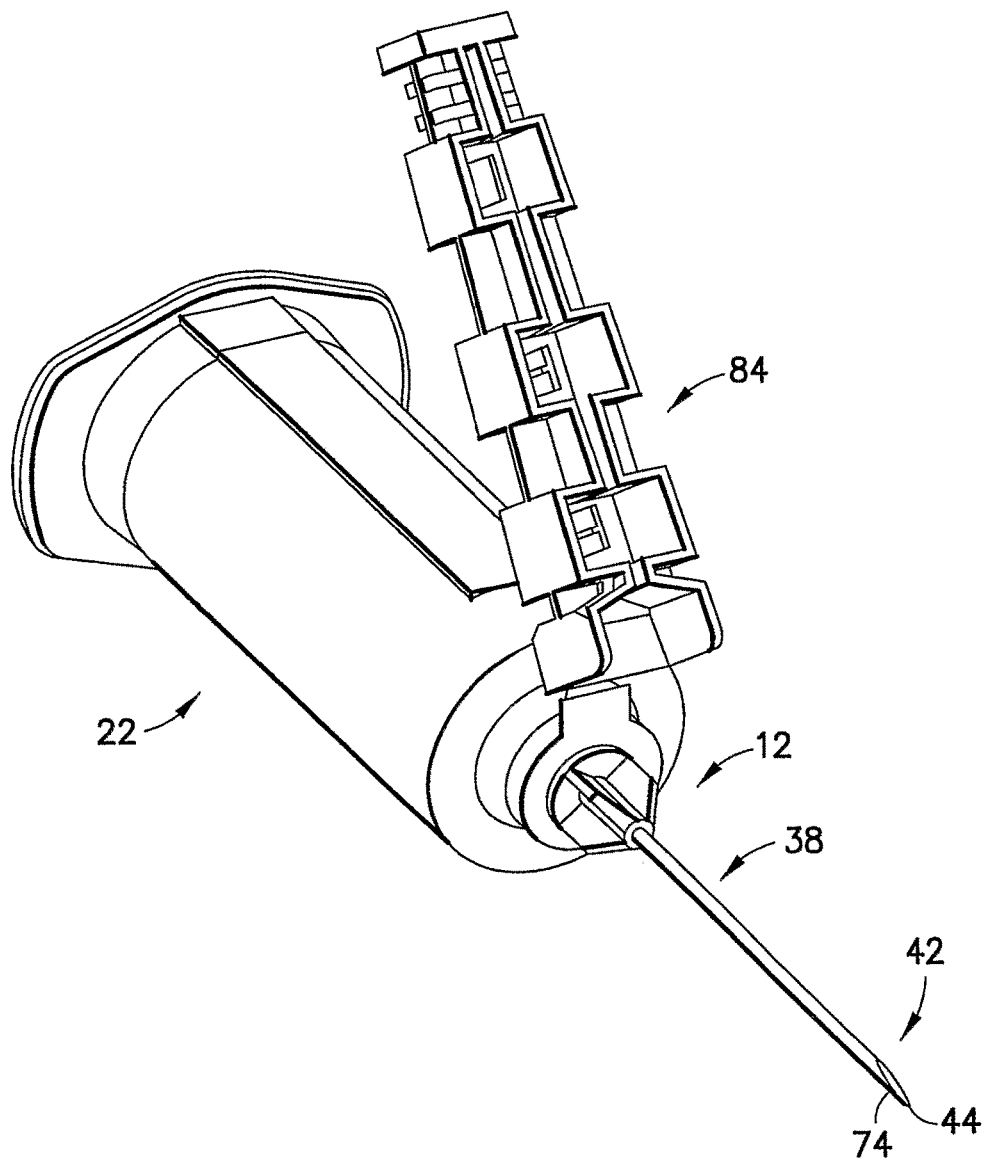
FIG. 12 is a perspective view of the hub, holder housing and pivotal shield of FIG. 11.
Figure 13:
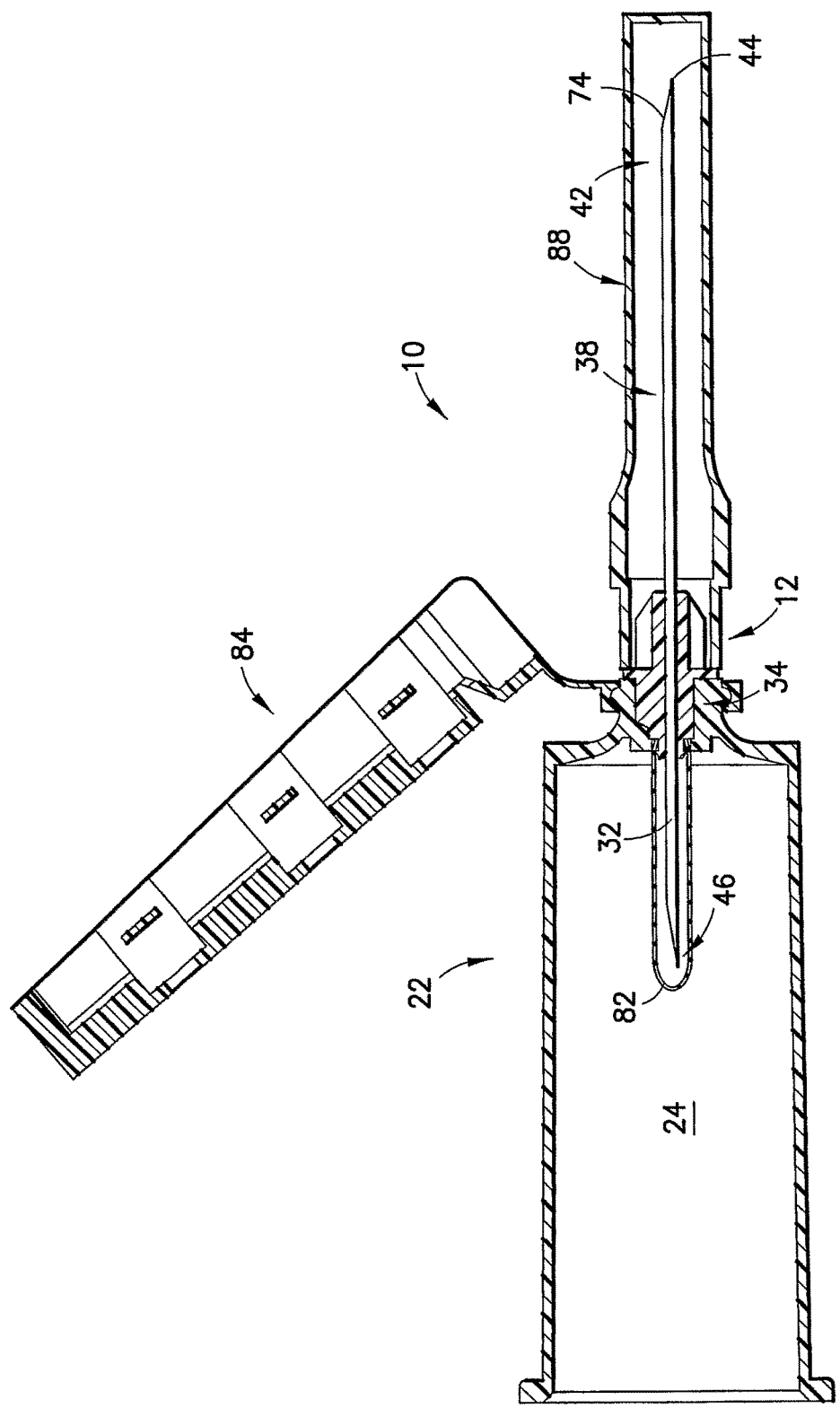
FIG. 13 is a side sectional view of the engaged structure of FIG. 12, together with a cap covering a portion of a needle.
Figure 14:
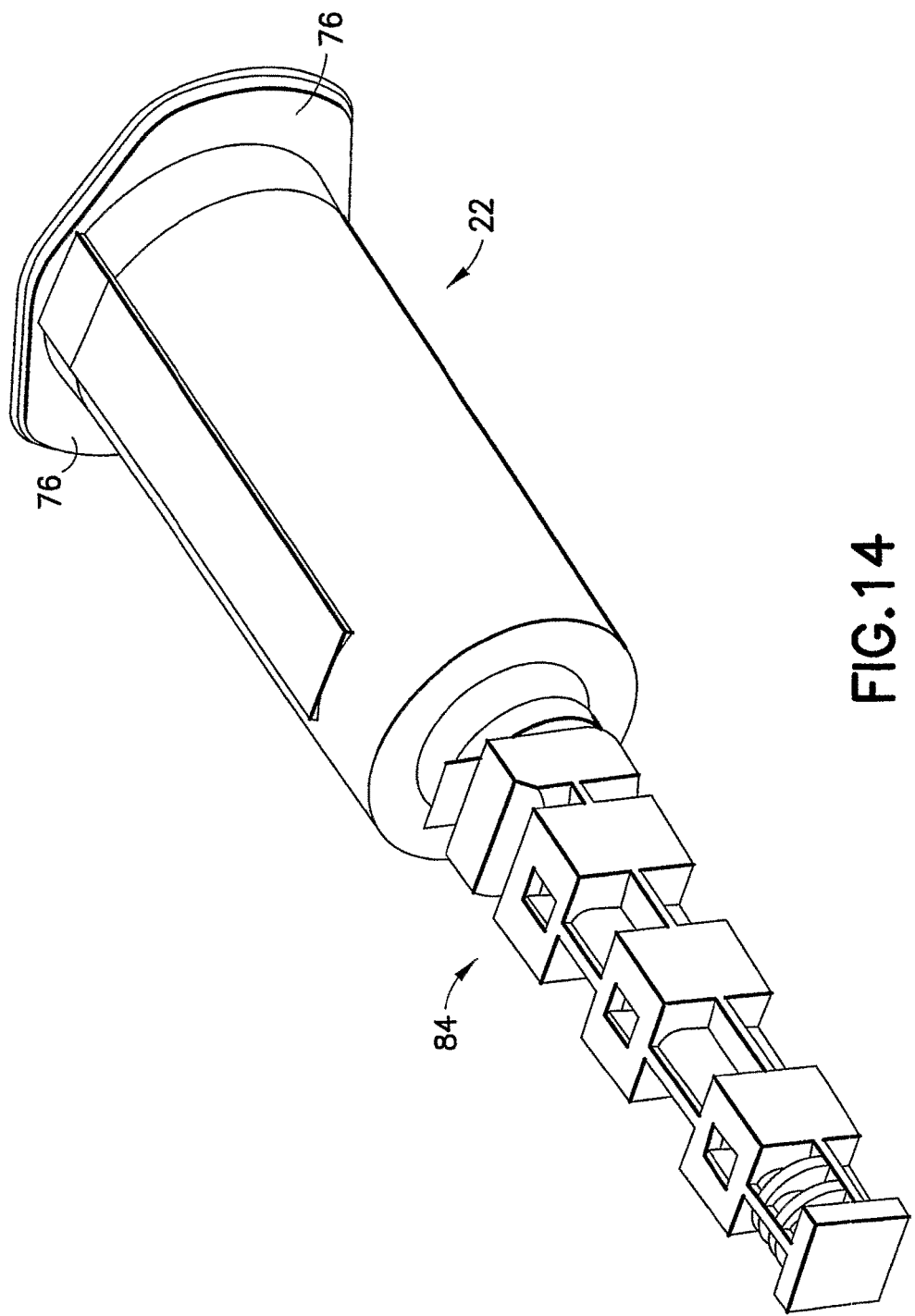
FIG. 14 is the perspective view of the structure of FIG. 12, with the pivotal shield encompassing the needle.

In a further embodiment depicted in FIGS. 11-14, the blood collection assembly 10 may include a shield 84 configured to encompass the intravenous end 42 of the needle cannula 38. This shield 84 may be removably attached to the hub 12 and/or the holder housing 22, or may be permanently affixed thereto or formed therewith. Shield 84 is desirably a pivotal shield, which is adapted to pivot between an open position in which the intravenous end 42 of the needle cannula 38 is exposed, as shown in FIG. 12, and a closed position encompassing or shielding the intravenous end 42 of the needle cannula 38 therein, as shown in FIG. 14. In such an embodiment, enclosure 88 may also be provided for sealing the needle cannula 38 therein prior to use.

Figure 8:
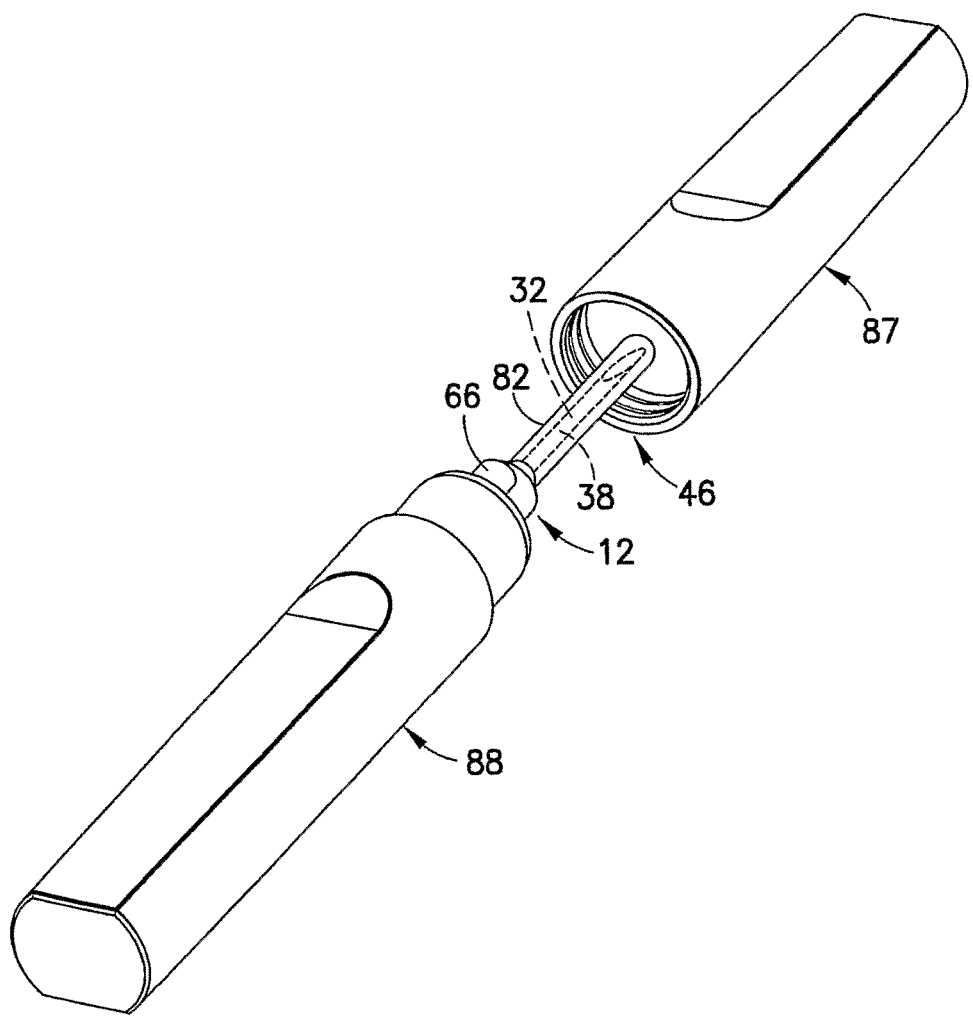
FIG. 8 is a perspective view of an enclosure.
Figure 9:
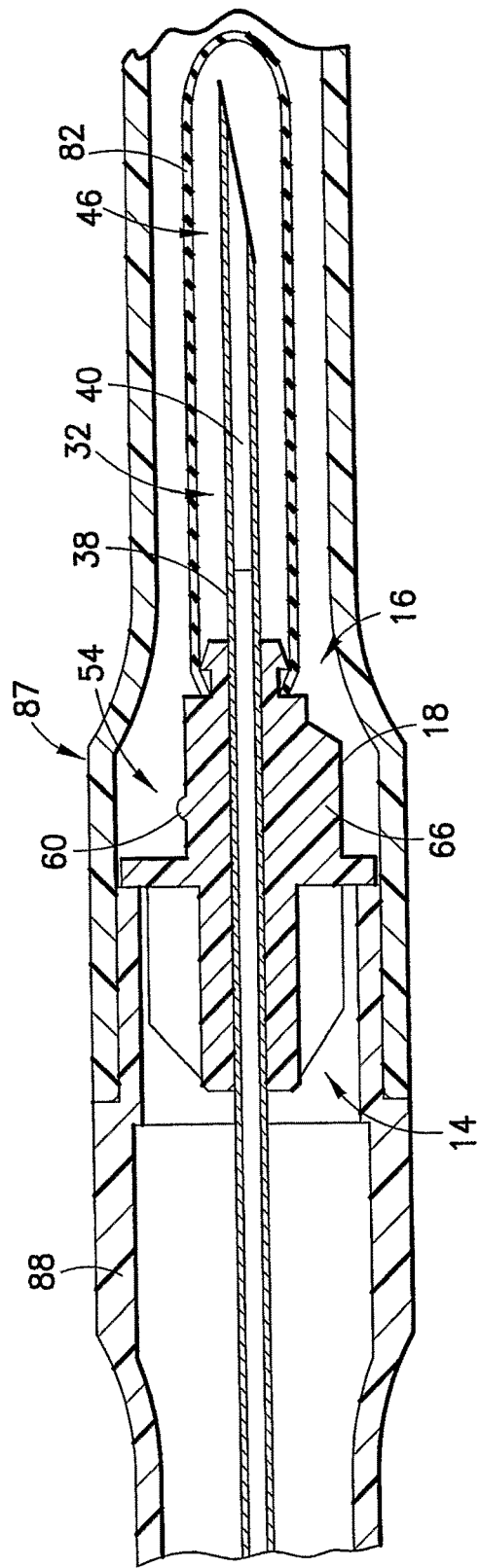
FIG. 9 is a side sectional view of the engaged enclosure surrounding the hub in FIG. 8.

Assembly of the blood collection assembly 10 will now be described. It is contemplated that needle assembly 11 may be provided as a disposable assembly as shown in FIGS. 8-9 for attachment with holder housing 22, which may be separate structures which are assembled immediately prior to use and disassembled after use, as is common practice in the field. As shown in FIGS. 8-9, such a needle assembly 11 may be provided with enclosure 88 covering the intravenous end 42 and affixed or fitted to hub 12, and with a separate rear cover 87 fitted therewith, whereupon the rear cover 87 can be removed and hub 12 assembled into holder housing 22 immediately prior to use. In order to reduce the risk of disease transmission, however, it is preferable that needle assembly 11 and holder housing 22 are provided as a pre-assembled structure with the needle assembly 11 attached to the holder housing 22 during manufacturing and assembly and prior to packaging.

In any event, needle assembly 11 is provided including the needle cannula 38 having a bevel 74 at the forward intravenous end 42, as discussed hereinabove, mounted to the hub 12. The protrusion 54 in this instance is located on the hub 12 and extends substantially perimetrically around the outer surface 18 of the hub 12 at its proximal end 16. In addition, in this embodiment, the nub 66 extends from the outer surface 18 at the proximal end 16 of the hub 12 adjacent protrusion 54, and is in alignment with the bevel 74 of the needle cannula 38. The holder housing 22 is provided, and this holder housing 22 may be arranged as discussed hereinabove. In particular, the receiving port 30 includes an internal surface 56 for mating with the protrusion 54, and a notch portion 68 for engagement with the nub 66. The proximal end 16 of the hub 12 is inserted into the receiving port 30 of the holder housing 22 through the forward end 28 thereof, with the nub 66 aligned with the notch portion 68. The outer surface 70 of the nub 66 and the corresponding internal surface 72 of the notch portion 68 may act together to guide the hub 12 into the proper alignment with respect to the holder housing 22, in a predetermined position. Such alignment between the nub 66 and the notch portion 68 occurs during the assembly process prior to the snap-fit engagement between the hub 12 and the holder housing 22.

The protrusion 54 of the hub 12 thereafter engages the corresponding mating internal surface 56 of the receiving port 30 substantially around an entire contacting or mating surface therebetween. In particular, the protrusion 54 which extends around the outer perimeter of the hub outer surface 18 engages into the groove 58 extending perimetrically within the corresponding surface 56 of the receiving port 30 in an interfering manner providing a snap fit engagement, with the nub 66 also engaged with the notch portion 68. Accordingly, insertion of the hub 12 within the receiving port 30 aligns the hub 12, and therefore, the needle cannula 38 to a predetermined position, such as with bevel 74 in an upright position for effective use with a patient, and also axially locks the hub 12 with the holder housing 22, in a snap-fit engagement. The blood collection assembly 10 assembled as such may further be provided with enclosure 88 protectively surrounding the intravenous end 42, and may be packaged in this manner for later use.

During use, the forward intravenous end 42 of the needle cannula 38 is inserted through the skin of a patient to obtain a sample using known blood collection procedures. After use, the forward intravenous end 42 of the needle cannula 38 is removed from the patient, and the pivoting shield 84, if provided, can be pivoted thereabout to protectively shield the needle. Shield 84 may include structure therein for engaging with the needle cannula 38 when rotated or pivoted to a safety position encompassing intravenous end 42 thereof, such as a cannula lock mechanism, thereby preventing the shield 84 from pivoting out of the shielding position once it has been moved into the shielding position. After shielding, the blood collection assembly 10 can be appropriately discarded in a medical waste container.

Figure 15:
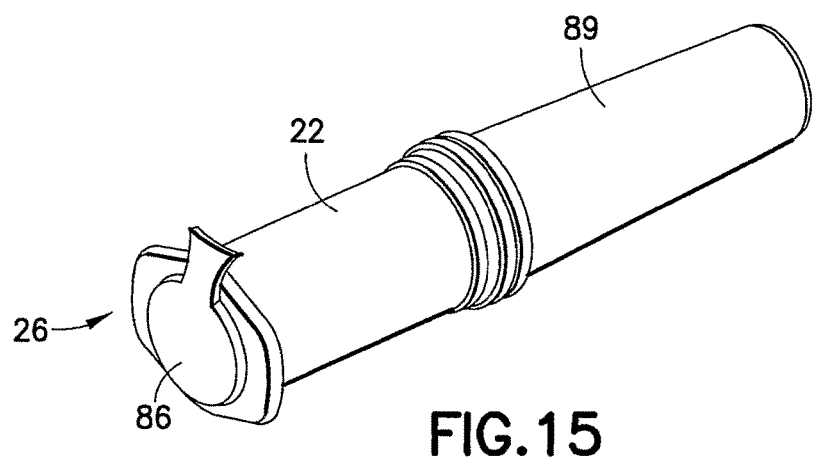
FIG. 15 is a perspective view of a blood collection assembly in a further embodiment, with a protective cover.
Figure 16:
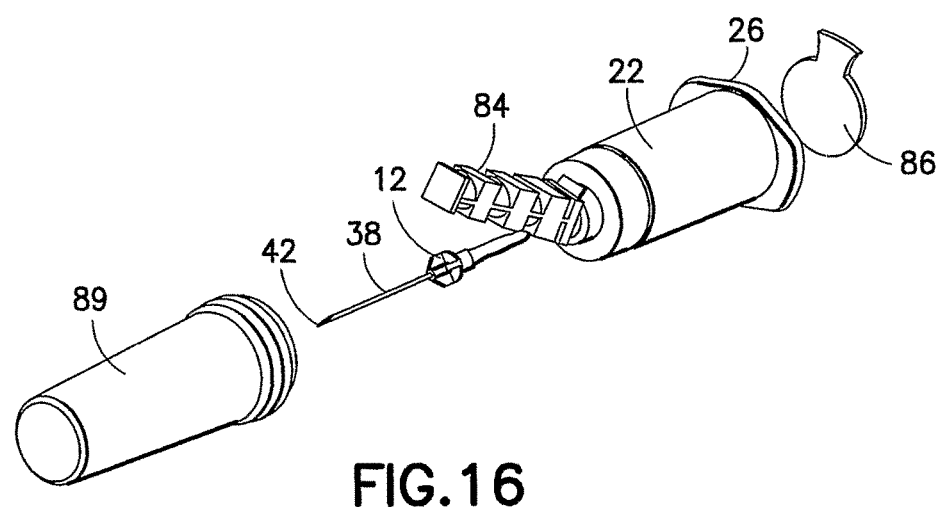
FIG. 16 is an exploded perspective view of the assembly of FIG. 15.

A further embodiment is depicted in FIGS. 15-16. In such an embodiment, holder housing 22 with hub 12 attached thereto and, optionally, with shield 84 also present, can be protectively packaged or covered within an enclosure 89. Enclosure 89 differs from enclosure 88 described above in that enclosure 89 is designed so as to attach directly to the outer surface of the holder housing 22, encompassing intravenous end 42 of the needle cannula 38 as well as the pivoting shield 84. The pivoting shield 84 can be contained within enclosure 89 without lockingly engaging needle cannula 38, such that when enclosure 89 is removed, pivoting shield 84 can be moved out of the way for use, and then pivoted to a locking position with the needle cannula 38 to encompass the puncture tip at he intravenous end 42 thereof. Also, a cap element 86 may be provided at the rearward end 26 of the holder housing 22, sealing the receiving chamber 24. In this manner, blood collection assembly 10 can be prepackaged and sterilized as a preassembled unit ready for use, without any assembly required by the phlebotomist prior to a procedure.

The blood collection assembly 10 of the present invention allows a needle assembly including a hub 12 to be "snap fit" with a holder housing 22. Therefore, in this manner, the structure of the blood collection assembly 10 of the present embodiments of the invention allows for a more efficient and easily engageable hub/holder housing assembly. Further, with the use of the anti-rotation element 64, both the holder housing 22 and the needle cannula 38, and in particular the bevel 74 of the cannula, may be appropriately aligned and also prevented from unwanted rotation. Also, the specific engagement of the interengaging structure between the hub 12 and the holder housing 22 provides support against torque applied to the hub to prevent disengagement. In particular, by providing the interengaging structure extending substantially perimetrically around the hub outer surface 18 and the surface 56 of the receiving port 30, such as annular rib 60 in interference engagement with groove 58 around the entire perimeter of the exterior of hub outer surface 18, continuous support is provided around the entire contacting surface. Also, the corresponding rounded profiles of the annular rib 60 and the groove 58 establish substantially continuous contacting surfaces between the hub 12 and the receiving port 30 at the point of interengagement therebetween. Moreover, with the annular rib 60 being located on the hub outer surface 18 between the distal end 14 and the proximal end 16, a portion of the hub outer surface 18 on either side of the annular rib 60 also provides a continuous contacting surface between the hub 12 and the receiving port 30, thereby providing further support against torque pressure. Such continuous contacting surfaces provide support at the point of engagement between the hub 12 and the annular rib 60 to retain the hub 12 secured to the holder housing 22 when torque forces are applied thereto. In particular, pivotal movement of the shield 84 to the shielding position to encompass the intravenous end 42 of the needle cannula 38 causes a torque force against needle cannula 38 which force is transferred to the distal end 14 of the hub 12. The continuous contacting surfaces, and in particular the interfering structure extending substantially perimetrically between the hub outer surface 18 and the receiving port 30 as described above, effectively retains the hub 12 secured to the holder housing 22 without risk of release of the snap-fit engagement therebetween.

While the assembly described is generally discussed herein in terms of several embodiments, the present disclosure is to be considered as exemplary of the principals of the invention and is not intended to limit the invention to the embodiments illustrated. Various modifications may be made by those of skilled in the art without departing from the scope and spirit of the present invention. The scope of the present invention is defined by the appended claims and their equivalents.

The invention claimed is:

1. A blood collection assembly, comprising:

a holder housing defining a receiving chamber and including a rearward end adapted to receive a sample collection tube within the chamber, a forward end including a receiving port having an interior surface, and a receiving structure formed within the interior surface of the receiving port, the receiving structure comprising a radial receiving portion comprising an annular groove extending perimetrically within the interior surface of the receiving port and dividing the interior surface into a first portion and a second portion and a longitudinal receiving portion; and a hub comprising a hub outer surface extending between a distal end and a proximal end, the hub further comprising an internal opening extending therethrough and a puncturing element at the proximal end thereof;

wherein the hub outer surface comprises a radial locking component and an anti-rotation member, the radial locking component comprising an annular protrusion extending perimetrically about the hub outer surface and dividing the outer surface of the hub into a first portion and a second portion and the anti-rotation member protruding from and extending longitudinally along the hub outer surface perpendicular to the radial locking component, wherein a first portion of the anti-rotation member extends from the first portion of the outer surface of the hub on one side of the annular protrusion in a longitudinal direction towards the distal end of the hub and a second portion of the anti-rotation member extends from the second portion of the outer surface of the hub on an opposite side of the annular protrusion in a longitudinal direction towards the proximal end of the hub, the annular protrusion intersecting the anti-rotation member, wherein upon receipt of the anti-rotation member within the receiving port, the anti-rotation member and the longitudinal receiving portion are adapted to align the hub and the holder housing in a predetermined position with respect to one another and are adapted to prevent rotational movement of the hub within the receiving port;

wherein, with the hub received within the receiving port of the holder housing, the radial locking component lockably engages the radial receiving portion and the anti-rotation member engages the longitudinal receiving portion thereby providing a snap-fit engagement for axially locking the hub to the holder housing with the puncturing element of the hub extending through the receiving port and into the chamber of the holder housing, and wherein the first portion of the interior surface of the receiving port contacts the first portion of the outer surface of the hub and the second portion of the interior surface of the receiving port contacts the second portion of the outer surface of the hub.

2. The assembly of claim 1, further comprising a needle cannula including an internal lumen mounted through the internal opening of the hub, the needle cannula having a forward intravenous end with a puncture tip extending from the distal end of the hub and a rearward non-patient end extending from the proximal end of the hub, the non-patient end comprising the puncturing element.

3. The assembly of claim 1, wherein the distal end of the hub comprises a mating surface adapted to engage a medical device having a complimentary mating surface.

4. The assembly of claim 1, wherein engagement between the radial locking component and the radial receiving portion, and the anti-rotation member and the longitudinal receiving portion, provides support against torque applied to the distal end of the hub, thereby preventing release of the snap-fit engagement between the hub and the holder housing.

5. The assembly of claim 1, wherein the annular protrusion comprises an annular rib.

6. The assembly of claim 1, wherein the anti-rotation member comprises a nub extending from the hub outer surface at the proximal end of the hub, and wherein the longitudinal receiving portion of the receiving port includes a notch portion configured to receive and abut an outer surface of the nub.

7. The assembly of claim 6, wherein the outer surface of the nub is rounded and configured for insertion within and abutment against a complimentary rounded internal surface of the notch portion of the receiving port.

8. The assembly of claim 2, wherein insertion of the anti-rotation member within the longitudinal receiving portion of the receiving port aligns the puncture tip of said intravenous end of the needle cannula to a predetermined position.

9. The assembly of claim 8, wherein the rearward end of the holder housing includes a pair of flanges extending from opposing sides thereof and a bottom surface of the holder housing is configured to rest on the patient's skin; wherein the puncture tip of the intravenous end of the needle cannula includes a bevel; and wherein insertion of the anti-rotation member within the longitudinal receiving portion of the receiving port aligns the bevel to a predetermined position with respect to the pair of flanges and the bottom surface of the holder housing.

10. The assembly of claim 9, wherein insertion of the anti-rotation member within the receiving port aligns the bevel between 60 degrees and 120 degrees from at least one of the pair of flanges.

11. The assembly of claim 8, further comprising a shield in pivotable engagement with at least one of the hub and the holder housing and adapted for pivotal movement to encompass the puncture tip of the needle cannula.

12. The assembly of claim 1, wherein the radial locking component and the anti-rotation member are configured to ensure continuous contact perimetrically between contacting surfaces of the hub and the holder housing to establish an axial lock and rotational fixation therebetween.

13. A blood collection assembly, comprising:

a needle assembly comprising a needle cannula having an intravenous end with a bevel puncture tip and a non-patient end mounted to a hub, the hub extending between a distal end and a proximal end and including a radial locking component and an anti-rotation member, the radial locking component comprising an annular protrusion extending perimetrically about a hub outer surface and dividing the hub outer surface into a first portion and a second portion and the anti-rotation member protruding from and extending longitudinally along the hub outer surface perpendicular to the radial locking component; and a holder housing defining a receiving chamber and including a rearward end adapted to receive a sample collection tube within the chamber, a forward end including a receiving port extending therethrough and configured to receive at least a portion of the hub in a snap fit engagement therein, the receiving port having an interior surface and a receiving structure formed within the interior surface of the receiving port, the receiving structure comprising a radial receiving portion comprising an annular groove extending perimetrically within the interior surface of the receiving port and dividing the interior surface into a first portion and a second portion, and a longitudinal receiving portion;

wherein a first portion of the anti-rotation member extends from the first portion of the outer surface of the hub on one side of the annular protrusion in a longitudinal direction towards the distal end of the hub and a second portion of the anti-rotation member extends from the second portion of the outer surface of the hub on an opposite side of the annular protrusion in a longitudinal direction towards the proximal end of the hub, the annular protrusion intersecting the anti-rotation member, wherein, upon receipt of the anti-rotation member within the receiving port, the anti-rotation member and the longitudinal receiving portion are adapted to align the hub and the holder housing in a predetermined position with respect to one another and to prevent rotational movement of the hub within the receiving port;

wherein, with the hub received within the receiving port of the holder housing, the radial locking component lockably engages the radial receiving portion and the anti-rotation member engages the longitudinal receiving portion thereby providing the snap-fit engagement between the hub and the holder housing and the first portion of the interior surface of the receiving port contacts the first portion of the outer surface of the hub and the second portion of the interior surface of the receiving port contacts the second portion of the outer surface of the hub.

14. The assembly of claim 13, wherein said rearward end of said holder housing comprises at least one flange for resisting rolling of said holder housing on a flat surface thereby defining an upper surface of said holder housing, and wherein insertion of said anti-rotation member within the longitudinal receiving portion of said receiving port aligns the bevel of said cannula to a predetermined range of angles with respect to said holder housing.

15. The assembly of claim 13, further comprising a shield in pivotable engagement with at least one of the hub and the holder housing for pivotal movement to encompass the intravenous end of the needle cannula.

16. The assembly of claim 13, wherein the radial locking component and the anti-rotation member are configured to ensure continuous contact perimetrically between contacting surfaces of the hub and the holder housing to establish an axial lock and rotational fixation therebetween.

17. A blood collection assembly, comprising:
a holder housing defining a receiving chamber and including a rearward end adapted to receive a sample collection tube within the chamber and a forward end including a receiving port having an interior surface;
a hub comprising a hub outer surface extending between a distal end and a proximal end, the hub further comprising an internal opening extending therethrough and a puncturing element at the proximal end thereof;
a locking anti-rotation element disposed on the hub outer surface, the locking anti-rotation element comprising a radial locking component and a longitudinal anti-rotation member, the radial locking component comprising an annular protrusion extending perimetrically about the hub outer surface adjacent the proximal end of the hub and the longitudinal anti-rotation member protruding from and extending longitudinally along the hub outer surface perpendicular to the radial locking component, wherein a first portion of the anti-rotation member extends from the first portion of the outer surface of the hub on one side of the annular protrusion in a longitudinal direction towards the distal end of the hub and a second portion of the anti-rotation member extends from the second portion of the outer surface of the hub on an opposite side of the annular protrusion in a longitudinal direction towards the proximal end of the hub, the annular protrusion intersecting the anti-rotation member; and
a receiving structure formed within the receiving port of the holder housing, the receiving structure comprising a radial receiving portion and a longitudinal receiving portion, the radial receiving portion for mating with the radial locking component of the hub comprises an annular groove extending perimetrically within the interior surface of the receiving port and divides the interior surface into a first portion and a second portion and the longitudinal receiving portion extends longitudinally within the interior surface of the receiving port for mating with the longitudinal anti-rotation member of the hub,
wherein, with the hub received within the receiving port of the holder housing such that the radial locking component of the hub is received within the radial receiving portion of the receiving structure and the longitudinal anti-rotation member of the hub is received within the longitudinal receiving portion of the receiving structure, the radial locking component is adapted to lock the hub to the holder housing with the puncturing element of the hub extending through the receiving port and into the chamber of the holder housing and the longitudinal anti-rotation member and the longitudinal receiving portion are adapted to prevent rotational movement of the hub within the receiving port of the holder housing and to align the hub and the holder housing in a predetermined position with respect to one another, and
the first portion of the interior surface of the receiving port contacts the first portion of the outer surface of the hub and the second portion of the interior surface of the receiving port contacts the second portion of the outer surface of the hub.

18. The assembly of claim 17, wherein the longitudinal anti-rotation member of the hub comprises a nub.

19. The assembly of claim 17, wherein the longitudinal receiving portion comprises a notch portion.

20. The assembly of claim 17, wherein the radial locking component and the anti-rotation member are configured to ensure continuous contact perimetrically between contacting surfaces of the hub and the holder housing to establish an axial lock and rotational fixation therebetween.

* * * * *